United States Patent [19]
Cheng et al.

[11] Patent Number: 5,869,461
[45] Date of Patent: Feb. 9, 1999

[54] REDUCING TOXICITY OF L-NUCLEOSIDES WITH D-NUCLEOSIDES

[75] Inventors: Yung-Chi Cheng, Woodbridge; Tai-Shun Lin, deceased, late of North Haven, both of Conn., by Pauline Lin, executrix

[73] Assignee: Yale University, New Haven, Conn.

[21] Appl. No.: 406,198

[22] Filed: Mar. 16, 1995

[51] Int. Cl.⁶ .......................... A61K 31/70; C07H 19/06; C07H 19/16
[52] U.S. Cl. ..................................... 514/43; 45/49; 45/50
[58] Field of Search ................................. 514/49, 50, 45, 514/43

[56] References Cited

U.S. PATENT DOCUMENTS

| | | |
|---|---|---|
| 3,817,982 | 6/1974 | Verheyden et al. . |
| 4,788,181 | 11/1988 | Driscoll et al. . |
| 4,861,759 | 8/1989 | Mitsuya et al. . |
| 4,879,277 | 11/1989 | Mitsuya et al. . |
| 5,128,458 | 7/1992 | Montgomery et al. . |
| 5,567,689 | 10/1996 | Sommadassi et al. . |

FOREIGN PATENT DOCUMENTS

| | | |
|---|---|---|
| 409 227 | 1/1991 | European Pat. Off. . |
| 587 364 | 3/1994 | European Pat. Off. . |
| 4 224 737 | 2/1994 | Germany . |
| 1-151 595 | of 1989 | Japan . |
| 1-100 191 | 4/1989 | Japan . |
| 1-143 892 | 6/1989 | Japan . |
| 2-069 476 | of 1990 | Japan . |
| 8 800 050 | 1/1988 | WIPO . |
| 9 001 036 | 2/1990 | WIPO . |
| 9 214 743 | 9/1992 | WIPO . |
| 9 220 696 | 11/1992 | WIPO . |
| 9 409 793 | 5/1994 | WIPO . |
| 9 414 456 | 7/1994 | WIPO . |
| 9 427 616 | 8/1994 | WIPO . |

OTHER PUBLICATIONS

Du, et al. Int. J. Cell Clon. 10:87 (1992).
Siddiqui, et al. J. Med. Chem. 35:2195 (1992).
Okabe, et al. J. Org. Chem. 56:4392 (1991).
Kim, et al. J. Med Chem. 30:862 (1987).
Lin, et al. J. Med. Chem. 37:798 (1994).
Chang, et al. J. Biol. Chem. 267:22414 (1992).
Chang, et al. J. Biol. Chem. 267:13938 (1992).
Mansuri, et al. Bioorg. Med. Chem. Let. 1:65, 1991.
Fujimore, et al., "A convenient & Stereoselective Synthesis," Nucleosides & Nucleotides 11 (2–4) pp. 341–349, 1992.
Doong, et al., "Inhibition of the Replication of Hepatitis B . . . , " Proc. Nat'l. Acad. Sci. USA, vol. 88, pp. 8495–8499, 1991.
Huang, et al., "A Facile Synthesis of 4'–Thio–2'–Deoxypyrimidine," Nucleosides & Nucleotides, 12(2), pp. 139–147, 1993.
Secrist, et al., "Synthesis & Anti–HIV Activity of 4'–thio . . . , " J. Med. Chem. vol. 35, pp. 533–538, 1992.
Secrist, et al., "Synthesis & Biological Activity of 2'–Deoxy . . . , " J. Med. Chem., vol. 34, pp. 2361–2366, 1991.
Barton, et al., "The Invention of Radical Reactions Part XXIX," Tetrahedron, vol. 49, No. 14, pp. 2793–2804, 1993.
Taniguchi, et al., "Stereochemical Studies—XXX," Tetrahedron, vol. 30, pp. 3547–3552, 1974.
Lin, et al., "Antiviral Activity of 2',3'–Dideoxycyridin–2'. . . , " Biochem. Pharm., vol. 36, No. 3, pp. 311–316, 1987.
Ravid, et al., "Synthesis of the Enantiomers of 4–Substituted . . . ," Tetrahedron, vol. 34, 1444–1452, 1978.
Hanessian et al., "Stereochemical Control of Nature's . . . ," Tetrahedron, vol. 43, No. 21, pp. 5055–5072, 1987.
Spadari et al., "L–thymidine is Phosphhorylated by Herpes," J. Med. Chem., vol. 34, pp. 4214–4220, 1992.
Horwitz et al., "Nucleosides XI . . . , " J. Organic Chem, vol. 32, pp. 817–818, 1967.
Di Bisceglie et al., "Hepatocellular Carcinoma . . . , " Annals Interm. Med., 1988, 108:390–401.
World Health Organization, "Progress in the Control of Viral Hepatitis," Bulletin of the WHO 66(4):443–455 (1988).
Chen and Cheng, "Delayed Cytotoxicity . . . , " J. Bio. Chem. vol. 264, No. 20, pp. 11934–11937, 1989.
Lardes et al., "Susceptibilities of Zidovudine–Susceptible . . . , " Antimicrobial Agents & Chemotherapy, vol. 34, No. 3, pp. 436–441, 1990.
Price et al., "Inhibition of the Replication of Hepatitis B . . . , " Proc. Nat'l. Acad. Sci. USA, vol. 86, pp. 8541–8544, 1989.
Suzuki et al., "Inhibition of Duck Hepatitis B . . . , " Biomed & Biophys. Res. Comm., vol. 156, No. 3, p. 1144, 1988.
Chang et al., "Deoxycytidine Deaminase–Resistant Stereoisomer . . . , " J. Bio. Chem., vol. 267, pp. 13938–13942, 1992.
Chang et al., "Biochemical Pharmacology . . . " J. Bio. Chem., vol. 267, No. 31, pp. 22414–22420, 1992.
Yokota et al., "Comparative Activities," Antimicrobial Agents & Chemotherapy, vol. 34, No. 7, pp. 1326–1330, 1990.
Beasley et al., "Hepatocellular Carcinoma and Hepatitis B Virus," The Lancet, Nov. 21, 1981, pp. 1129–1132.
Meisel et al., "Inhibition of Hepatitis B . . . , " J. Med. Virology 30:137–141 (1990).

(List continued on next page.)

*Primary Examiner*—Gary L. Kunz
*Attorney, Agent, or Firm*—Henry D. Coleman; R. Neil Sudol

[57] ABSTRACT

The present invention relates to novel methods for reducing toxicity associated with the administration of conventional "D" nucleoside compounds, including anti-HIV nucleosides and related therapeutic agents. Therapeutic methods which rely on conventional "D" nucleosides exhibit unexpectedly reduced toxicity when the methods include the co-administration of effective amounts of "L" nucleoside compounds. The method are particularly useful for the treatment of HIV infections and AIDS related symptoms in humans.

20 Claims, 3 Drawing Sheets

OTHER PUBLICATIONS

Coates et al., "The Separated Enantiomers of 2'–Deoxy–3'–thiacytidine . . . ," Antimicrobial Agents and Chemotherapy, Jan. 1992, pp. 202–205.

Schinazi et al., "Activities of the four Optical Isomers . . . ," Antimicrobial Agents and Chemotherapy, Mar. 1992, pp. 672–676.

Lin et al., J. Med. Chem. 37, 798 (1994).

REDUCING TOXICITY OF L-NUCLEOSIDES WITH D-NUCLEOSIDES

FIELD OF THE INVENTION

The present invention relates to novel methods for reducing toxicity associated with the administration of conventional "D" nucleoside compounds, including anti-HIV nucleosides and related therapeutic agents. Therapeutic methods which rely on conventional "D" nucleosides exhibit unexpectedly reduced toxicity when the methods include the co-administration of effective amounts of "L" nucleoside compounds. The method are particularly useful for the treatment of HIV infections and AIDS related symptoms in humans.

BACKGROUND OF THE INVENTION

The use of various nucleoside analogs as agents for the treatment of cancer, fungal infections, bacterial infections and viral infections is not new. Most of the present therapies involving nucleoside analogs rely on nucleosides which generally have a natural "D" configuration about the sugar synthon. Although there are a number of reasons for the limitations associated with the use of nucleoside analogs as therapeutic agents including unfavorable pharmacokinetics and lack of specificity, it is the underlying toxicity of the therapeutic nucleoside analogs to the host which is perhaps primarily responsible for the limited use of these agents. One of the primary mechanisms for nucleoside toxicity in humans is by inhibition of mitochondrial DNA synthesis.

In the treatment of viral infections, the treatment of Herpes Simplex Virus (HSV), related Herpes infections and Human Immunodeficiency Virus (HIV) with nucleoside analogs is now part of the armamentarium of the medical practitioner. A viral disease which recently has been studied ingreat detail and treated with only limited success is AIDS. AIDS is a generally fatal disease caused by a human pathogenic retrovirus known as human T-lymphotropic virus type III (HTLV III), lymphadenopathy-associated virus (LAV) or human immunodeficiency virus (HIV).

A number of nucleosides have played important roles in developing a treatment regimen for HIV infections. 3'-azido-3'deoxythymidine (AZT) is a prime example, although recent reports raise some doubts about its effectiveness. A number of 2',3'-dideoxynucleoside analogs also have exhibited significant activity against human immunodeficiency virus (HIV), including 3'-deoxy-2',3'-didehydrothymidine (D4T), carbocyclic analog of 2',3'-dideoxy-2',3'-didehydroguanosine (Carbovir), 2',3'-dideoxycytidine (ddC), 3'-azido-2',3'-dideoxyguanosine (AZG), 2',3'-dideoxyinosine (DDI), 2',3'-dideoxy-2',3'-didehydrocytidine (D4C), 3'-fluoro-2',3'-dideoxyadenosine, 3'-fluoro-3'-deoxythymidine and 3'-azido-2',3'-dideoxyuridine. See, for example, Larder, et al., *Antimicrob. Agents Chemother.*, 34, 436 (1990).

A number of the above-described nucleoside analogs have shown some promise in the treatment of AIDS or as inhibitors of HIV. These include 3'-azido-3'deoxythymidine (AZT) as well as the $\beta$-D-2',3'-Dideoxynucleosides, for example, $\beta$-D-2',3'-dideoxycytidine (ddC) and $\beta$-D-2',3'-dideoxyadenosine and $\beta$-D-2,'3'-dideoxyinosine (DDI), among other nucleosides (Richman, et al., *N. Engl. J. Med.*, 317, 192, 1987; and Mitsuya, *Proc. Nat. Acad. Sci. USA*, 83, 1911, 1986). Other nucleoside agents which are at various clinical states of use for the treatment of HIV include $\beta$-D-2',3'-didehydro-3'-deoxy-thymidine (D4T), 3'-azido-2', 3'-dideoxyuridine (AzddU, CS-87, AZDU) and 3'-fluoro-3'-deoxythymidine (FLT).

In currently available therapeutics, the only approved compounds for use as anti-HIV agents alone are AZT and DDI (generally, DDI is administered to those patients who, for some reason, are intolerant to the administration of AZT). An aDDItional agent, ddC, has received approval for use as an anti-HIV agent in combination with AZT.

All of the above described anti-HIV nucleoside agents are used in the form of their naturally occuring enantiomers (D sugars). All of the approved anti-HIV nucleoside agents exhibit significant side effects in the form of toxicity. In aDDItion, resistance to these agents has recently emerged.

Thus, the search has continued to find agents which exhibit significant anti-HIV activity with reduced toxicity. Recent developments have focused on certain nucleoside analogs having an unnatural "L" configuration about the sugar synthon rather than the natural "D" configuration. These agents, especially $\beta$-L-2',3'-dideoxycytidine ($\beta$-L-ddC) and $\beta$-L-5-fluoro-2',3'-dideoxycytidine ($\beta$-L-FddC) have exhibited anti-HIV activity. At the same time that these "L" nucleoside analogs exhibit significant anti-HIV activity, in vivo studies have shown these same nucleoside analogs to exhibit significantly reduced toxicity to the host compared to anti-HIV nucleoside agents based upon the natural "D" configuration of the sugar synthon. Further studies evidence that a combination of an effective amount of at least one of the "D" nucleoside analogs with a toxicity reducing amount of at least one nucleoside compound having the unnatural "L" configuration produces a therapeutic composition exhibiting unexpectedly reduced toxicity to the host. In those instances where the "L" nucleoside has the same therapeutic activity as the "D" nucleoside analog to be administered, the result will be a therapeutic effect will be an increased therapeutic activity in combination with unexpectedly diminished toxicity. The unexpected reduction of toxicity caused by nucleoside compounds having the natural "D" configuration of the sugar synthon is a primary feature of the present invention.

OBJECT OF THE INVENTION

It is an object of the present invention to provide a method for reducing the toxicity of nucleoside compounds having a natural "D" configuration about the sugar synthon which are therapeutically useful as anti-viral agents, anti-cancer agents, anti-microbial agents and anti-fungal agents.

It is an additional object of the present invention to provide novel combinations of "D" nucleoside compounds and "L" nucleoside compounds which exhibit enhanced therapeutic activity and reduced toxicity to the host.

It is yet another object of the present invention to provide a method to limit toxicity during the administration of D-nucleoside therapeutic agents caused at least in part by the inhibition of mitochondrial DNA synthesis.

It is a further object of the present invention to provide a method of reducing the toxicity associated with the administration of anti-HIV nucleosides having the natural "D" configuration.

It is still an additional object of the present invention to provide a novel method of treating HIV infections using a combination of anti-HIV agents which exhibit enhanced anti-HIV activity and reduced toxicity to the host.

These and other objects of the present invention may be readily gleaned from a reading of the description of the invention which follows.

SUMMARY OF THE INVENTION

The present invention relates to the unexpected discovery that the co-administration of a nucleoside compound having the "L" configuration about the sugar synthon in combination with a nucleoside compound having the "D" configuration about the sugar synthon will significantly reduce the toxicity to the patient caused by administration of the "D" nucleoside compound.

The present invention, therefore, relates to a method for significantly reducing the toxicity in a patient associated with the administration of a therapeutically effective amount of a "D" nucleoside compound, said "D" nucleoside compound causing substantial toxicity to said patient at said effective amount, the method comprising co-administering a toxicity reducing effective amount of at least one "L" nucleoside compound in combination with a therapeutically effective amount of said "D" nucleoside compound. "D" nucleosides which may be used in the present invention include the anti-cancer compounds 9-β-D-arabinofuranosyladenosine ("ARA A"), 2-Fluoro-9-β-D-arabinofuranosyladenosine ("2-Fluoro ARA A"), β-D-arabinofuranosylcytidine ("ARA C"), 2'-difluoro-2'-deoxycytidine (Gemcitabine), (E)-2'-deoxy-2'-(fluoromethylene)cytidine, 2-chloro-2'-deoxyadenosine ("CDA"), 2'-Fluoro-9-β-D-arabinofuranosylthymidine ("FMAU") and 2'-Fluoro-5-Iodo-9-β-D-arabinofuranosyluridine ("FIAU"), among others. Preferred "D" nucleoside compounds for use in the present invention include the anti-HIV nucleoside compounds 3'-azido-3'deoxythymidine (AZT) as well as the β-D-2',3'-dideoxynucleosides, for example, β-D-2',3'-dideoxycytidine (ddC), β-D-2',3'-dideoxyadenosine, β-D-2,'3'-dideoxyinosine (DDI) and β-D-2',3'-didehydro-3'-deoxythymidine (D4T). Preferred "L" nucleoside compounds for use in the present invention include β-L-2',3'-dideoxycytidine (β-L-ddC), β-L-5-Fluoro-2', 3'-dideoxycytidine (β-L-FddC), β-L-2'-deoxy-3'-thiacytidine [(—)3TC] and β-L-5-Fluoro-2'-deoxy-3'-thiacytidine [(—)FTC], among others.

The present method is well suited for therapeutic treatment of cancer, fungal infections and microbial infections including viral infections and bacterial infections where "D" nucleoside compounds are used in therapeutically effective amounts and produce substantial toxicity to the patient being treated.

The present invention also relates to a pharmaceutical composition comprising a therapeutically effective amount of a "D" nucleoside compound, said D-nucleoside compound substantially inhibiting mitochondrial DNA synthesis in a patient to be administered said composition, in combination with a toxicity reducing effective amount of an "L" nucleoside.

Compounds according to the present invention may be used as agents for the treatment of cancer, viral infections, certain types of fungal infections, microbial infections and/or related disease states. Among the "D" nucleosides useful in the present invention include "D" nucleosides which may be used in the present invention include the anti-cancer compounds 9-β-D-arabinofuranosyladenosine ("ARA A"), 2-Fluoro-9-β-D-arabinofuranosyladenosine ("2-Fluoro ARA A"), β-D-arabinofuranosylcytidine ("ARA C"), 2'-difluoro-2'-deoxycytidine (Gemcitabine), (E)-2'-deoxy-2'-(fluoromethylene)cytidine, 2-chloro-2'-deoxyadenosine ("CDA"), 2'-Fluoro-9-β-D-arabinofuranosylthymidine ("FMAU") and 2'-Fluoro-5-Iodo-9-β-D-arabinofuranosyluridine ("FIAU"), among others. Preferred "D" nucleoside compounds for use in the present compositions include anti-HIV nucleoside compounds AZT, ddC, β-D-2',3'-dideoxyadenosine, DDI and D4T. Preferred "L" nucleoside compounds for use in the present compositions include β-L-ddC, β-L-FddC, (—)3TC and (—)FTC, among others. Preferred pharmaceutical compositions for use in the present invention are useful in treating viral infections, especially including HIV infections.

The present invention also relates to the unexpected discovery that the co-administration of an anti-HIV effective amount of a first nucleoside compound having the natural "D" configuration about the sugar synthon in combination with an effective amount of a second nucleoside compound having an unnatural "L" configuration about the sugar synthon will provide additive or synergistic anti-HIV activity and unexpectedly reduced toxicity associated with the "D" nucleoside.

In conformance with this invention, pharmaceutical compositions are disclosed comprising anti-HIV effective amounts of a nucleoside compound having the natural "D" configuration and further comprising toxicity reducing effective amounts of a nucleoside compound having the unnatural "L" configuration about the sugar synthon. It is noted that in a number of embodiments according to the present invention, a toxicity reducing effective amount of the nucleoside having the unnatural "L" configuration may be more or less than the amount required of that same "L"-nucleoside to produce a therapeutic effect which is unrelated to the toxicity reducing effect. For example, in the treatment of HIV infections, a toxicity reducing effective amount of the "L" nucleoside β-L-5-Fluoro-2',3'-dideoxycytidine (β-L-FddC) may be less than one-half (preferably, about one-fourth to about one-half) the therapeutically effective dosage of this agent, which itself exhibits significant anti-HIV and anti-HBV activity.

Methods for reducing the toxicity associated with the administration of traditional anti-HIV nucleoside agents are therefore contemplated by the present invention.

DETAILED DESCRIPTION OF THE INVENTION

Figure 1:
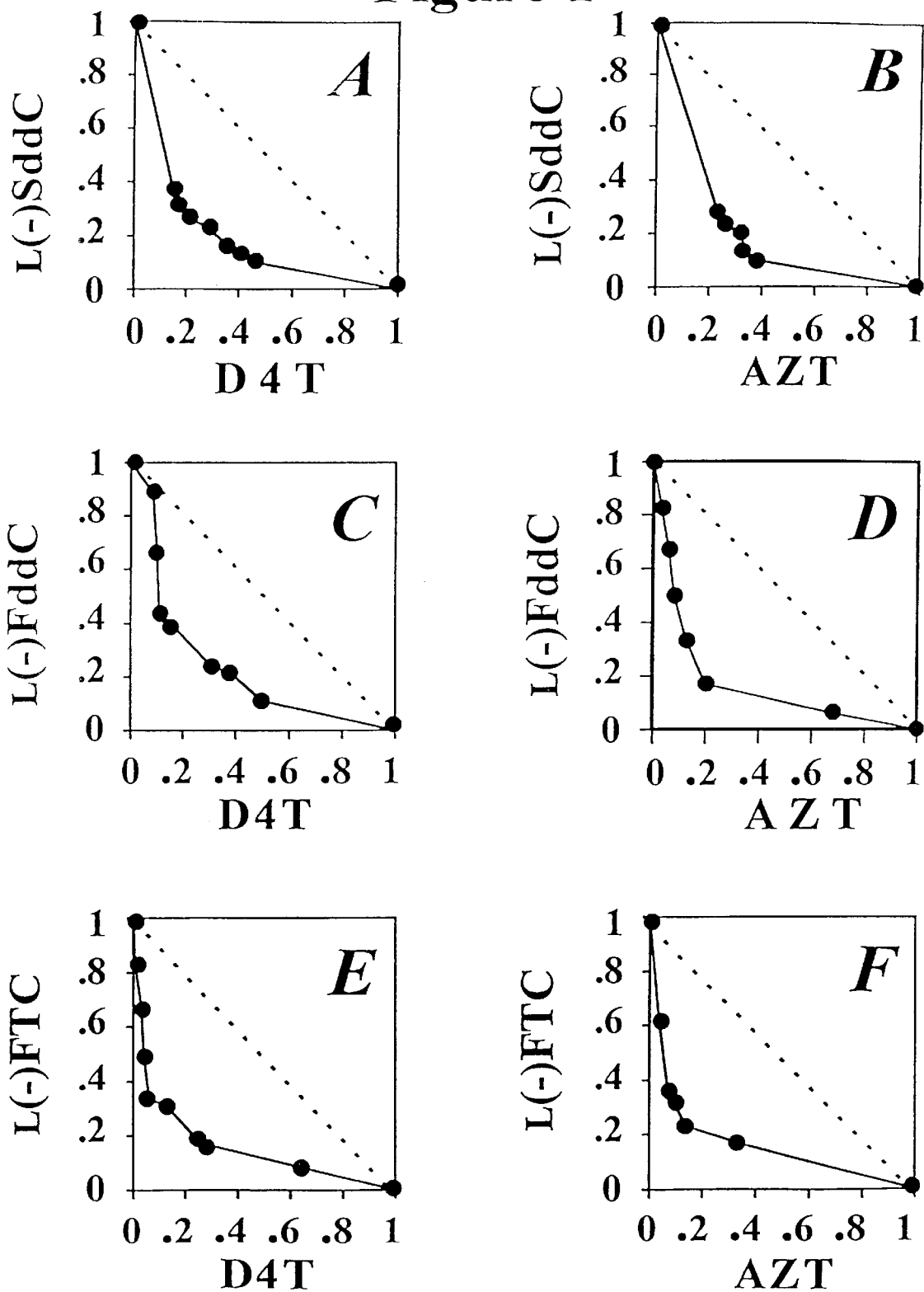
FIGS. 1A–1F and 2A–2F are isobolograms depicting the effect of co-administration of L-nucleosides on the $ID_{50}$ value of a number of nucleoside analogs. Isobolograms are plotted as the percent change in the $ID_{50}$ of L-nucleosides (B-L-FddC or B-L-SddC or L-FTC) at various concentrations when in combination with AZT, D4T (FIG. 1), ddC or ddI (FIG.2) at varying concentrations on the x-axis plotted against the percent change in the $ID_{50}$ value of AZT, D4T, ddC or ddI at various concentrations in combination with L-nucleosides (B-L-FddC or B-L-SddC or L-FTC) varying concentrations on the y-axis.

The following definitions will be used throughout the specification to describe the present invention.

The term "inhibitory effective concentration" or "inhibitory effective amount" is used throughout the specification to describe concentrations or amounts of nucleoside compounds according to the present invention which substantially or appreciably inhibit the growth or replication of susceptible cancerous cells or organisms, including fungi, bacteria and viruses, especially including HIV.

The term "therapeutic effective concentration" or "therapeutically effective amount" is used throughout the specification to describe concentrations or amounts of compounds according to the present invention which are therapeutically effective in treating cancer or infections caused by fungi, bacteria or viruses including hepatitis B virus (HBV), especially including HIV infections in humans. The terms inhibitory effective concentration, inhibition effective amount, therapeutic effective concentration and therapeutically effective amount are all interrelated terms which may be synonymous, depending upon the infection or disease state treated and the therapeutic result desired.

The term "toxicity reducing effective amount" is used throughout the specification to describe amounts of L-nucleosides which are co-administered with D-nucleosides to produce significant reduction in the toxicity associated with the administration of a D-nucleoside.

The term "L-configuration" is used throughout the specification to describe the chemical configuration of the ribofuranosyl moiety of compounds according to the present invention. The L-configuration of the sugar moiety of compounds of the present invention is an unnatural configuration, i.e., it is generally not found in nature and contrasts with the D-configuration of ribose sugar moieties of the naturally occurring nucleosides cytidine, adenosine, thymidine, guanosine and uridine.

The term "L-nucleoside" is used throughout the specificaton to describe those nucleoside compounds used in the present invention which have an L-configuration of the pentosyl (ribofuranosyl, deoxyribofuranosyl, dideoxyribofuranosyl, arabinosyl or other pentosyl) moiety in contrast to the natural D-configuration. L-nucleoside compounds for use in the present invention generally have a β anomeric chemical linkage between the nucleoside base and the pentosyl moiety. Compounds according to the present invention may contain natural or synthetic nucleic acid bases including adenine, guanine, cytosine, thymine and uracil and substituted derivatives of these bases. Compounds of the present invention may also contain modification of the (pentosyl (ribofuranosyl, deoxyribofuranosyl, dideoxyribofuranosyl, arabinosyl or other pentosyl) moiety. β-L-2',3'-dideoxynucleosides are particularly preferred for use in the present invention. Exemplary preferred L-nucleosides according to the present invention include β-L-2',3'-dideoxycytidine (β-L-ddC), β-L-5-Fluoro-2',3'-dideoxycytidine (β-L-FddC), β-L-2'-deoxy-3'-thiacytidine [(—)3TC] and β-L-5-Fluoro-2'-deoxy-3'-thiacytidine [(—)FTC]. L-nucleoside compounds according to the present invention include their pharmaceutically acceptable derivatives such as pharmaceutically acceptable salts and related prodrug forms.

The term "D-configuration" is used throughout the specification to describe the natural chemical configuration of the pentosyl (ribofuranosyl, deoxyribofuranosyl, dideoxyribofuranosyl, arabinosyl, or other pentosyl) moiety of compounds according to the present invention. The D-configuration of the sugar moiety of compounds of the present invention is a natural configuration, i.e., it is generally found in nature and is exemplified by the sugar moieties of the naturally occuring nucleosides cytidine, adenosine, thymidine, guanosine and uridine.

The term "D-nucleoside" is used throughout the specification to describe the nucleoside compounds used in the present invention which have the natural D-configuration of the pentosyl (ribofuranosyl, deoxyribofuranosyl, dideoxyribofuranosyl, arabinosyl, or other pentosyl) moiety, in contrast to the unnatural L-configuration of the pentosyl moiety of L-nucleosides. D-nucleoside compounds for use in the present invention generally have a β anomeric chemical linkage between the nucleoside base and the ribofuranosyl moiety. D-nucleoside compounds according to the present invention are generally synthetic nucleoside compounds containing modification of the nucleic acid bases including adenine, guanine, cytosine, thymine and uracil and/or modification of the naturally occurring ribofuranosyl moiety. "D" nucleosides which may be used in the present invention include the anti-cancer compounds 9-β-D-arabinofuranosyladenosine ("ARA A"), 2-Fluoro-9-β-D-arabinofuranosyladenosine ("2-Fluoro ARA A"), β-D-arabinofuranosylcytidine ("ARA C"), 2'-difluoro-2'-deoxycytidine (Gemcitabine), (E)-2'-deoxy-2'-(fluoromethylene)cytidine, 2-chloro-2'-deoxyadenosine ("CDA"), 2'-Fluoro-9-β-D-arabinofuranosylthymidine ("FMAU") and 2'-Fluoro-5-Iodo-9-β-D-arabinofuranosyluridine ("FIAU"), among others. Other exemplary D-nucleosides for use in the present invention include the D-nucleoside compounds having activity against HIV. 3'-azido-3'deoxythymidine (AZT) as well as the β-D-2',3'-dideoxynucleosides, for example, β-D-2',3'-dideoxycytidine (ddC), β-D-2',3'-dideoxyadenosine, β-D-2,'3'-dideoxyinosine (DDI) and β-D-2',3'-didehydro-3'-deoxythymidine (D4T). D-nucleoside compounds according to the present invention include their pharmaceutically acceptable derivatives such as pharmaceutically acceptable salts and related prodrug forms.

The term "nucleoside compound" is used throughout the specification to describe the active compositions according to the present invention, whether they be therapeutically active D-nucleoside compounds or alternatively, toxicity reducing or toxicity reducing and therapeutically active L-nucleoside compounds. As used herein nucleoside compounds include their pharmaceutically acceptable derivatives such as pharmaceutically acceptable salts and related prodrug forms. Nucleoside compounds according to the present invention are themselves active or are metabolized by the patient to an active metabolite derived from the originally administered nucleoside compound.

The term "patient" is used throughout the specification to describe an animal, including a human to whom treatment with the compositions according to the present invention is provided. For treatment of those infections, conditions or disease states which are specific for a specific animal such as a human patient, the term patient refers to that specific animal.

The term "pharmaceutically acceptable derivative" is used throughout the specification to describe any pharmaceutically acceptable salt or prodrug form (such as an ester or salt of an ester) of a nucleoside compound which, upon administration to a patient, provides directly or indirectly the nucleoside compound or an active metabolite of the nucleoside compound. Pharmaceutically acceptable salts include those derived from pharmaceutically acceptable inorganic or organic bases and acids. Suitable salts include those derived from inorganic acids such as hydrochloric acid, phosphoric acid, hydrobromic acid, sulphuric acid, nitric acid, perchloric acid, organic acids such as fumaric acid, maleic acid, glycollic acid, lactic, acid, salicylic acid, succinic acid, tartaric acid, acetic acid, ctiric acid, formic acid, benzoic acid, malonic acid, alkali metals such as potassium and sodium, alkaline earth metals such as calcium, magnesium and ammonium salts, among numerous other acids well known in the pharmaceutical art.

The present invention relates to a method for decreasing the toxicity associated with the administration of therapeutically effective amounts of a D-nucleoside compound. The method comprises administering in combination with a therapeutically effective amount of one or more of said D-nucleoside(s) a toxicity reducing effective amount of an L-nucleoside compound, the combination of the D-nucleoside compound and the L-nucleoside compound exhibiting a toxicity level which is significantly lower than the toxicity exhibited when the D-nucleoside compound is administered alone at the same concentration it is administered in combination with the L-nucleoside compound. This is an unexpected result.

The present invention also relates to therapeutic methods for the treatment of cancer, fungal infections, bacterial infections and viral infections including HBV (especially including retroviral infections such as HIV infections) using therapeutically effective amounts of D-nucleoside compounds in combination with toxicity reducing effective amounts of an L-nucleoside compound. In this therapeutic method, a D-nucleoside may be administered in greater amounts within a therapeutically effective dosage range to a patient suffering from a disease or condition to be treated by the D-nucleoside compound. This result occurs because the co-administration of an L-nucleoside actually reduces the toxicity caused by the D-nucleoside compound.

The present invention also relates to a therapeutic method for the treatment of HIV infections comprising administering a therapeutically effective amount of at least one D-nucleoside compound selected from the group consisting of β-D-3'-azido-3'deoxythymidine (AZT), β-D-2',3'-dideoxycytidine (ddC), β-D-2,'3'-dideoxyinosine (DDI) and β-D-2',3'-didehydro-3'-deoxy-thymidine (D4T) in combination with a toxicity reducing effective amount of an L-nucleoside selected from the group consisting of β-L-2', 3'-dideoxycytidine (β-L-ddC), β-L-5-Fluoro-2',3'-dideoxycytidine (β-L-FddC), β-L-2'-deoxy-3'-thiacytidine [(—)3TC] β-L-5-Fluoro-2'-deoxy-3'-thiacytidine [(—)FTC], and mixtures, thereof. Preferred anti-HIV compositions include combinations of at least two D-nucleoside agents selected from the group consisting of AZT, ddC, DDI and D4T in combination with one of more L-nucleoside compounds selected from the group consisting of β-L-ddC, β-L-FddC, (—)3TC or (—)FTC.

Pharmaceutical compositions according to the present invention include a therapeutically effective amount of a D-nucleoside in combination with a toxicity reducing effective amount of an L-nucleoside. The D-nucleoside compounds which may be used in the present invention according to the present invention are therapeutically useful as anti-cancer agents, anti-fungal agents, anti-bacterial agents and anti-viral agents (especiallly including HIV. Among the D-nucleoside compounds which may be used in the present invention include "D" nucleosides which may be used in the present invention include the anti-cancer compounds 9-β-D-arabinofuranosyladenosine ("ARA A"), 2-Fluoro-9-β-D-arabinofuranosyladenosine ("2-Fluoro ARA A"), β-D-arabinofuranosylcytidine ("ARA C"), 2'-difluoro-2'-deoxycytidine (Gemcitabine), (E)-2'-deoxy-2'-(fluoromethylene)cytidine, 2-chloro-2'-deoxyadenosine ("CDA"), 2'-Fluoro-9-β-D-arabinofuranosylthymidine ("FMAU") and 2'-Fluoro-5-Iodo-9-β-D-arabinofuranosyluridine ("FIAU"), among others.

D-nucleosides used as antiviral agents are primarily useful for their anti-retroviral activity and in particular, their anti-HIV activity. In general, the most preferred anti-HIV D-nucleoside compounds include AZT, ddC, DDI and D4T. These are generally used to treat HIV infections by administering therapeutically effective amounts of these agents to a patient suffering from an HIV infection. These D-nucleoside compounds, in combination with an effective amount of an L-nucleoside according to the present invention, exhibit significantly less toxicity than when administered alone.

Accordingly, combinations of D-nucleoside compounds and L-nucleoside compounds according to the present invention are useful as prophylactic agents for the prevention of a variety of infections and/or disease states including cancer, fungus infections, bacterial infections and viral infections, especially including retroviral infections such as HIV infections.

Combinations of the compounds as described above, in pharmaceutical dosage form, may be used as prophylactic agents, because of the reduced toxicity which occurs when D-nucleosides are administered with L-nucleosides according to the present invention. These pharmaceutical compositions may be particularly appropriate as antiviral agents, and in particular, anti-HIV agents. Because of its toxicity reducing effect in combination with D-nucleosides, and because of its significant anti-HIV activity, B-L-FddC is an especially effective L-nucleoside to be combined with any one or more anti-HIV D-nucleoside compounds as a therapeutically effective compound for inhibiting HIV and preventing AIDS or as a prophylactic composition for preventing HIV infections. Combinations of L-nucelosides such as β-L-FddC and D-nucleosides AZT, ddD, DDI or D4T may be used to treat HIV infections, with a combination of AZT, D4T and β-L-FddC being a preferred embodiment.

D-nucleoside compounds useful in the present invention include those readily available in the art. The L-nucleoside compounds according to the present invention are produced by synthetic methods which are readily known to those of ordinary skill in the art and include standard chemical synthetic methods as fully described in the literature (See, for example, Lin, et al., *J. Med. Chem.*, 37, No. 6, 1994; PCT Application PCT/US94/05790, W094/27616; Mansuri, et al., *Biorganic and Medicinal Chemistry Letters*, 1, 65–68, 1991; Beach, et al. *J. Org. Chem.*, 57, 2217, 1992; and Hoong, et al., *J. Org. Chem.*, 57, 5563 1992; among others. In the case of L-nucleosides, synthesis of these compounds generally proceeds by condensing a previously synthesized nucleoside base onto the appropriate sugar synthon which will ultimately give rise to a nucleoside analog having the desired pentosyl moiety of L-configuration. Depending upon the synthetic pathway chosen, minor amounts (generally, less than 5–10% and preferably less than about 5% by weight) of D-nucleosides may be included in a given sample of L-nucleoside synthesized. Most preferably, the L-nucleoside analogs are substantially pure (contain insignificant quantities of D-nucleoside compunds).

The therapeutic aspect according to the present invention relates to methods for treating retroviral infections in animal or human patients, in particular, HBV or HIV infections in humans comprising administering anti-viral effective amounts of the compounds according to the present invention to inhibit the growth or replication of the viruses in the animal or human patient being treated.

Pharmaceutical compositions based upon these novel chemical compounds comprise the above-described compounds in a therapeutically effective amount for treating a viral, preferably retroviral including a HIV infection, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formation, esterification, etc., as previously described) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the D-nucleoside and L-nucleoside compounds, especially including acylated (acetylated or other esterified) derivatives, pyridine esters and various pharmaceutically acceptable salt forms of the present compounds may be preferred. One of ordinary skill in the art will recognize how to readily modify the present compounds to other pharmaceutically acceptable forms of the active nucleosides according to the present invention such as pro-drug forms to facilitate delivery of active compounds to a targeted site within the host organism or patient. The routineer also will take advantage of favorable pharmacokinetic parameters of these various drug forms, where applicable, in delivering the present compounds to a targeted site within the host organism or patient to maximize the intended effect of the compound.

The amount of D-nucleoside compound included within the therapeutically active compositions according to the present invention is an effective amount for treating the infection or condition, in its most preferred embodiment, an HIV infection. In the case of an HIV infection, the amount of a nucleoside compound chosen is that amount which will inhibit the growth or replication of HIV in the patient. This effective concentration will also, in many instances, help to diminish the time and/or the likelihood that AIDS related conditions such as AIDS-related complex (ARC) will become manifest in the patient. In contrast, the amount of L-nucleoside compound included within these active compositions is a toxicity reducing effective amount.

In certain instances, the L-nucleoside to be administered in combination with the D-nucleoside is also therapeutically effective against the infection, disease state or condition to be treated within the same dosage range for reducing toxicity of the co-administered D-nucleoside. In the case of the use of β-L-FddC in combination with at least one other D-nucleoside for the treatment of HIV infections, β-L-FddC in a toxicity reducing effective amount is generally included. A toxicity reducing amount of β-L-FddC according to this aspect of the present invention may be less than about one-half (preferably, about one-fourth to about one-half) the typical therapeutically effective amount of FddC given as an anti-HIV agent.

In general, a therapeutically effective amount of a D-nucleoside compound in dosage form according to the present invention is an effective amount for treating the infection or condition. In general, a daily dose usually ranges from less than about 1 mg./kg to about 1 g./kg or more, depending upon the condition or infection treated and the route of administration. Preferably, the dosage range is about 1 mg. to about 500 mg. per kg., which dosage form is given orally from 1 to 4 or more times per day. Administration of the pharmaceutical compositions according to the present invention may range from continuous (intravenous drip) to several oral administrations per day (for example, Q.I.D.) and may include oral, topical, parenteral, intramuscular, intravenous, sub-cutaneous, buccal and suppository administration, among other routes of administration.

In the case of HIV infections, typical D-nucleosides such as AZT, ddC, DDI and D4T are administered within the dosage range of about 1 mg./kg to about 500 mg/kg. per day, more preferably about 5 mg/kg. to about 100 or more mg/kg per day. In the case of the administration of AZT, because of the potency of this D-nucleoside, administration of about 5 mg/kg to about 50 mg/kg per day is typical (about 20 mg/kg for the typical 70 kg patient). The other D-nucleosides are administered in amounts which generally are at or above the range for AZT.

In the case of the co-administration of the L-nucleoside, the amount of L-nucleoside to be administered ranges from about 1 mg/kg. of the patient to about 500 mg/kg. or more of the patient or considerably more, depending upon the D-nucleoside compound to be co-administered, the L-nucleoside compound used to reduce the toxicity of the D-nucleoside, the condition or infection treated and the route of administration. In the case of HIV infections, the L-nucleoside compound is preferably administered in amounts ranging from about 100 ug/kg (micrograms per kilogram) to about 500 mg/kg. In the case of the use of β-L-FddC as an anti-HIV agent, the compound is preferably administered in an amount ranging from about 1 mg/kg to about 50 mg/kg, generally depending upon the pharmacokinetics of the agent in the patient. This dosage range generally produces effective blood level concentrations of active compound in the patient. In general, the weight ratio of D-nucleoside to L-nucleoside to be administered ranges from about 5:1 to about 1:10 or more, with preference for administration of L-nucleoside in an amount at least equal to (preferably, greater) the amount of D-nucleoside administered up to about three times the amount of D-nucleoside administered.

Administration of the nucleoside compounds according to the present invention may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the D-nucleoside compounds according to the present invention in combination with a toxicity reducing effective amount of an L-nucleoside compound is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives and excipients including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

In particularly preferred embodiments according to the present invention, the compounds and compositions are used to treat viral infections of mammals, including humans for HBV and HIV infections, and in particular, HIV infections in humans. In treating HIV infections, the compound β-L-FddC is effectively used to treat HIV infections, including AIDS, and is administered in oral dosage form in amounts ranging from about 50 mg. up to about 500 mg. or more up to six times a day (four hours a day, 4–6 times a day). The present compounds are preferably administered orally, but may be administered parenterally, topically or in suppository form.

The compounds according to the present invention, because of their unexpectedly low toxicity to host cells, may advantageously be employed prophylactically to prevent infection or to prevent the occurrence of clinical symptoms associated with the viral infection. Thus, the present invention also encompasses methods for the therapeutic or prophylactic treatment of fungal, bacterial or viral infections, and in particular HIV infections and for the prevention of the reoccurrence or relapse of a cancerous state. This prophylactic method comprises administering to a patient in need of such treatment an amount of a compound according to the present invention containing an amount of a D-nucleoside effective for alleviating, and/or preventing the infection, disease state or condition in combination with an L-nucleoside in an amount effective for reducing the toxicity ot the D-nucleoside. In this aspect of the present invention, it is particularly preferred that the pharmaceutical composition which is used should be maximally effective against the infection, disease state or condition to be treated and should exhibit a minimum of toxicity to the patient.

In the case of treating HIV infections, a preferred L-nucleoside, β-L-FddC in a toxicity reducing amount is co-administered with a therapeutically effective amount of any one or more of AZT, ddC, DDI or D4T for the therapeutic treatment of HIV or as a prophylactic agent to prevent the rapid proliferation of HIV or alternatively, to prolong the onset of AIDS in a patient. A preferred embodiment includes the co-administration of therapeutically effective amounts of AZT and D4T in combination with a toxicity reducing effective amount of β-L-FddC. An additional preferred embodiment includes the co-administration of AZT and ddC in combination with β-L-FddC.

In addition, the pharmaceutical compositions and methods according to the present invention may be utilized in combination with other agents to enhance a therapeutic treatment. Certain compounds according to the present invention may be effective for enhancing the biological activity of certain agents according to the present invention by reducing the metabolism or inactivation of other compounds and as such, are co-administered for this intended effect.

While not being limited by way of theory, it is believed that the L-nucleosides or their respective L-nucleotides may function to inhibit transport of the toxic D-nucleoside or their respective D-nucleotides into the mitochondria or other cellular structure where these agents inhibit DNA synthesis (for example, mitochondrial DNA synthesis), become misincorporated into mitochondrial DNA or otherwise interfere with the normal mitochondrial functions to produce toxicity to the patient. Inhibition by the L-nucleoside of D-nucleoside toxicity also appears to be dose dependent. Based upon the initial experiments, the co-administration of an L-nucleoside with a D-nucleoside will reduce the toxicity of virtually any D-nucleoside or D-nucleotide which produces toxicity by inhibiting mitochondrial DNA synthesis, becoming misincorporated into mitochondrial DNA or otherwise interferes with normal mitochondrial functions.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Example 1- Effect on $ID_{50}$ of Co-Administration of D-Nucleosides and L-Nucleosides The following anti-HIV drugs were tested in combination with the L-nucleoside β-L-5-fluoro-2',3'-dideoxycytidine [β-L-FddC or L(—)FddC]: 3'-azido-3'deoxythymidine (AZT) as well as the β-D-2',3'-dideoxynucleosides, for example, β-D-2',3'-dideoxycytidine (ddC), β-D-2',3'-dideoxyadenosine, β-D-2',3'-dideoxyinosine (DDI) and β-D-2',3'-didehydro-3'-deoxy-thymidine (D4T). β-L-FddC was obtained following the method of Lin, et al., *J. Med. Chem.*, 37, no. 6 (1994). AZT was obtained from Sigma Chemical Co., St. Louis, Mo., U.S.A. ddC was obtained from Aldrich Chemical Co., Milwaukke, Wis. U.S.A. DDI and D4T were obtained from Bristol-Myers Co., Wallingford. Conn., USA.

The above-mentioned drugs were tested using MT-2 cells infected with HIV-$1_{IIIB}$ as described by J. W. Mellers, et al., *Molecular Pharm.* 41, 446–451 (1991) with some modification. Briefly, triplicate wells of 96-well plates containing $1 \times 10^4$ MT-2 cells were infected with HIV-$1_{IIIB}$ at a multiplicity of infection (MOI) of 0.1 $TCID_{50}$ per cell ($TCID_{50}$— 50% tissue culture infective dose). Serial dilutions of drug were added immediately after infection. Cell viability was quantitated 5 days after infection by the MTT-dye reduction model (Larder, et al. *Antimicrob. Agents Chemother.* 34, 436–441, 1990) The eprcentage of protection was calculated with the formulat [(a—b/c—b)×100], in which a=the $A_{570}$ of drug-treated, virus-infected well, b =$A_{570}$ of no-drug infected wells, and c=$A_{570}$ of no-drug, uninfected wells. The drug $IC_{50}$ (50% inhibitory dose) was calculated from linear-$\log_{10}$ plots of the percentage of protection versus drug concentration. The calculated $ID_{50}$ values were as follows:

| | | |
|---|---|---|
| AZT | = | 0.2 uM (micromoles) |
| DDI | = | 14 uM |
| ddC | = | 0.6 uM |
| D4T | = | 4.0 uM |
| β-L-FddC | = | 2.0 uM |

Isobolograms (FIG. 1) were plotted as the percent change in the $ID_{50}$ of β-L-FddC at various concentrations in combination with AZT, D4T, ddC or DDI at varying concentations on the x-axis and vice versa on the y-axis.

Conclusion: This experiment evidences that the inclusion of the L-nucleoside β-L-FddC decreases the $ID_{50}$ of a co-administered D-nucleoside and vice versa, but that the effect tends to be additive with ddC and DDI and synergistic with AZT and D4T.

Example 2- Effect of β-L-FddC On the Cell Growth Inhibition of Anti-HIV Nucleoside Analogs CEM, a Human T-type lymohoblast tumor cell line was used for this study. The cells are seeded at $\times 10^5$ cells per ml. with a concentrated RPMI cell medium with 10% dialyzed fetal bovine serum in the presence of the drugs as indicated in Table 1, below. At the end of four days after the addition of the drug, the cell number was estimated by hemocytometer. Under the general conditions (RPMI cell medium as indicated with no drug added), the number of cells increase up to $1.2 \times 10^6$ cells per ml. The data, presented below, are normalized against the control The parenthetical values represent the expected effect the combined agents should have on cell growth.

TABLE 1

| β-L-FddC | Cell Growth- % of Control | | | | | |
|---|---|---|---|---|---|---|
| | ddC (uM) | | | | | |
| (luM) | 0 | 0.01 | | 0.1 | | 1.0 |
| -- | 100 | 93 | | 93 | | 79 |
| ++ | 84 | 88 | (78) | 84 | (78) | 76 (66) |
| | d4T (uM) | | | | | |
| | 0 | 0.3 | | 3.0 | | 30 |
| -- | 100 | 98 | | 84 | | 70 |
| ++ | 84 | 86 | (82) | 75 | (71) | 68 (59) |
| | AZT (uM) | | | | | |
| | 0 | 0.5 | | 5.0 | | 50 |
| -- | 100 | 91 | | 89 | | 74 |
| ++ | 84 | 80 | (76) | 79 | (75) | 75 (62) |
| | ddI (uM) | | | | | |
| | 0 | 50 | | 100 | | 200 |
| -- | 100 | 88 | | 85 | | 78 |
| ++ | 84 | 84 | (74) | 80 | (71) | 75 (65) |

Example 3- Effect of β-L-FddC on the Action of D4T or ddC on mtDNA Content

Mitochondrial DNA (mtDNA) content was determined by the method of Chen, et al., *J. Biol. Chem.*, 264, 11934–11937, 1989. Briefly, CEM cells were seeded at $1 \times 10^5$ cells per ml. in RPMI 1640 medium supplemented with 10% dialyzed FBS. To determine the effect of nucleoside analogues on mtDNA content, CEM cells were treated with various concentrations of drug 8 days with medium and drug changes every 2 days. Cells ($1 \times 10^5$) are washed twice with phosphate buffered serum (PBS) and resuspended in 25 mM Tris (pH 8.0) and 1 mM EDTA. The cells are lysed by 5 cycles of freeze/thaw. RNAase A (DNase free, final concentration of 0.1 mg/ml) is added to the cel ysate and incubated for 3 hours at 50° C. The lysate is brought to a final concentration of 10×SSC, boiled for 10 min., and applied to a nylon membrane presoaked in 2×SSC using a slot blot apparatus. The blots are hybridized as previously described (Chen, et al., 1989, supra.). To detect the mtDNA, a 880 base mtDNA fragment (spanning nucleotide positions 13,370 to 14,258) is labelled with a Stratagene random primer kit. All blots are normalized for loading using an Alu probe (ATCC). Blots are exposed to X-ray film and quantitated using a Molecular Dynamics Personal Densitometer SI. Values represent percentage of control of a typical experiment and are presented in Table 2, below.

TABLE 2

Effect of β-L-FddC and D4T or ddC on mtDNA Content

| | Percent mtDNA Content β-L-FddC (uM) | | |
|---|---|---|---|
| Compound | 0 | 0.5 | 2.0 |
| β-L-FddC | 100 | 87 | 98 |
| 15 uM D4T | 81 | 103 | 92 |
| 40 uM D4T | 48 | 72 | 77 |
| 0.01 uM ddC | 60 | 81 | nd* |
| 0.05 uM ddC | 28 | nd | 61 |

*nd- Not Determined

CONCLUSIONS

1). β-L-FddC could prevent the effect of AZT, ddC, DDI or D4T in inhibiting the synthesis of mitochondrial DNA synthesis.

2). The administration of β-L-FddC appears to inhibit the ability of the co-administered D-nucleoside to inhibit the synthesis of mitochondrial DNA, a mechanism which appears to be at least partly responsible for delaying the toxicity associated with the administration of AZT, ddC, DDI and D4T.

3). The co-administration of β-L-FddC reduces the $ID_{50}$ value of AZT, ddc, DDI and D4T, either additively (ddC or DDI) or synergistically (AZT or D4T) and also reduces the toxicity associated with the administration of these agents.

It is to be understood by those skilled in the art that the foregoing description and examples are illustrative of practicing the present invention, but are in no way limiting. Variations of the detail presented herein may be made without departing from the spirit and scope of the present invention as defined by the following claims.

It is claimed:

1. A method for reducing toxicity associated with the administration of a D-nucleoside compound which inhibits mitochondrial DNA synthesis in a patient, becomes misincorporated into mitochondrial DNA or interferes with the normal mitochondrial functions to produce toxicity in a patient, said method comprising co-administering with said D-nucleoside compound a toxicity reducing effective amount of a β-L-nucleoside compound selected from the group consisting of β-L-2',3'-dideoxycytidine, β_L-5-Fluoro-2',3'dideoxycytidine, β-L-2'-deoxy-3'-thiacytidine, β-L-5-Fluoro-2'-deoxy-3'-thiacytidine and mixtures thereof.

2. The method according to claim 1 wherein said D-nucleoside compound is selected from the group consisting of 9-β-D-arabinofuranosyladenosine, 2-Fluoro-9-β-D-arabinofuranosyladenosine, β-D-arabinofuranosylcytidine, 2'-difluoro-2'-deoxycytidine, (E)-2'-deoxy-2'-(fluoromethylene)cytidine, 2-chloro-2'-deoxyadenosine, 2'-Fluoro-9-β-D-arabinofuranosylthymidine and 2'-Fluoro-5-Iodo-9-β-D-arabinofuranosyluridine.

3. The method according to claim 1 wherein said D-nucleoside comprises therapeutically effective amounts of at least two compounds selected from the group consisting of AZT, ddC, DDI and D4T.

4. The method according to claim 3 wherein said L-nucleoside compound is β-L-2',3'-dideoxycytidine or β-L-5-Fluoro-2',3'-dideoxycytidine.

5. The method according to claim 3 wherein said L-nucleoside is β-L-5-Fluoro-2',3'-dideoxycytidine.

6. The method according to claim 1 wherein said β-L-2',3'-dideoxynucleoside is β-L-2',3'-dideoxycytidine or β-L-5-Fluoro-2',3'-dideoxycytidine.

7. The method according to claim 1 wherein said β-L-2',3'-dideoxynucleoside is β-L-5-Fluoro-2',3'-dideoxycytidine.

8. A method of treating an HIV infection in a patient comprising administering an effective amount of an anti-HIV D-nucleoside compound selected from the group consisting of AZT, ddI, ddC, D4T and mixtures, thereof to inhibit the growth or replication of HIV in said patient in combination with a toxicity reducing effective amount of a β-L-nucleoside compound selected from the group consisting of β-L-2',3'-dideoxycytidine, β-L-5-Fluoro-2',3'-dideoxycytidine, β-L-2'-deoxy-3'-thiacytidine, β-L-5-Fluoro-2'-deoxy-3'-thiacytidine and mixtures thereof, said β-L-nucleoside compound reducing the toxicity associated with the administration of said D-nucleoside compound.

9. The method according to claim 8 wherein said D-nucleoside comprises therapeutically effective amounts of at least two compounds selected from the group consisting of AZT, ddC, DDI and D4T.

10. The method according to claim 9 wherein said L-nucleoside compound is β-L-2',3'-dideoxycytidine or β-L-5-Fluoro-2',3'dideoxycytidine.

11. The method according to claim 9 wherein said L-nucleoside is β-L-5-Fluoro-2',3'-dideoxycytidine.

12. The method according to claim 8 wherein said β-L-2',3'-dideoxynucleoside compound is β-L-2',3'-dideoxycytidine or β-L-5-Fluoro-2',3'-dideoxycytidine.

13. The method according to claim 8 wherein said β-L-2',3'-dideoxynucleoside is β-L-5-Fluoro-2',3'-dideoxycytidine.

14. A pharmaceutical composition comprising a combination of a therapeutically effective amount of a D-nucleoside compound which inhibits mitochondrial DNA synthesis in said patient, becomes misincorporated into mitochondrial DNA or interferes with the normal mitochondrial functions to produce toxicity in a patient and a toxicity reducing effective amount of a β-L-nucleoside compound selected from the group consisting of β-L-2',3'-dideoxycytidine, β-L-5-Fluoro-2',3'dideoxycytidine, β-L-2'-deoxy-3'-thiacytidine, β-L-5-Fluoro-2'-deoxy-3'-thiacytidine and mixtures thereof.

15. The composition according to claim 14 wherein said D-nucleoside is selected from the group consisting of 9-β-D-arabinofuranosyladenosine, 2-Fluoro-9-β-D-arabinofuranosyladenosine, β-D-arabinofuranosylcytidine, 2'-difluoro-2'-deoxycytidine, (E)-2'-deoxy-2'-(fluoromethylene)cytidine, 2-chloro-2'-deoxyadenosine, 2'-Fluoro-9-β-D-arabinofuranosylthymiidne and 2'-Fluoro-5-Iodo-9-β-D-arabinofuranosyluridine.

16. The composition according to claim 14 wherein said D-nucleoside compound comprises therapeutically effective amounts of at least two compounds selected from the group consisting of AZT, ddC, DDI and D4T.

17. The composition according to claim 16 wherein said L-nucleoside compound is β-L-2',3'-dideoxycytidine or β-L-5-Fluoro-2',3'-dideoxycytidine.

18. The composition according to claim 16 wherein said L-nucleoside compound is β-L-5-Fluoro-2',3'-dideoxycytidine.

19. The composition according to claim 14 wherein said β-L-2',3'-dideoxynucleoside compound is β-L-2',3'-dideoxycytidine or β-L-5-Fluoro-2',3'-dideoxycytidine.

20. The composition according to claim 14 wherein said β-L-2',3'-dideoxynucleoside is β-L-5-Fluoro-2',3'-dideoxycytidine.

* * * * *

UNITED STATES PATENT AND TRADEMARK OFFICE
CERTIFICATE OF CORRECTION

PATENT NO. : 5,869,461

DATED : February 9, 1999

INVENTOR(S) : Cheng, et al.

It is certified that error appears in the above-indentified patent and that said Letters Patent is hereby corrected as shown below:

Title page, item [54] and column 1, lines 1-2:

Change "D-Nucleosides' to --L-Nucleosides-- and "L-Nucleosides" to --D-Nucleosides--.

Figure 2:
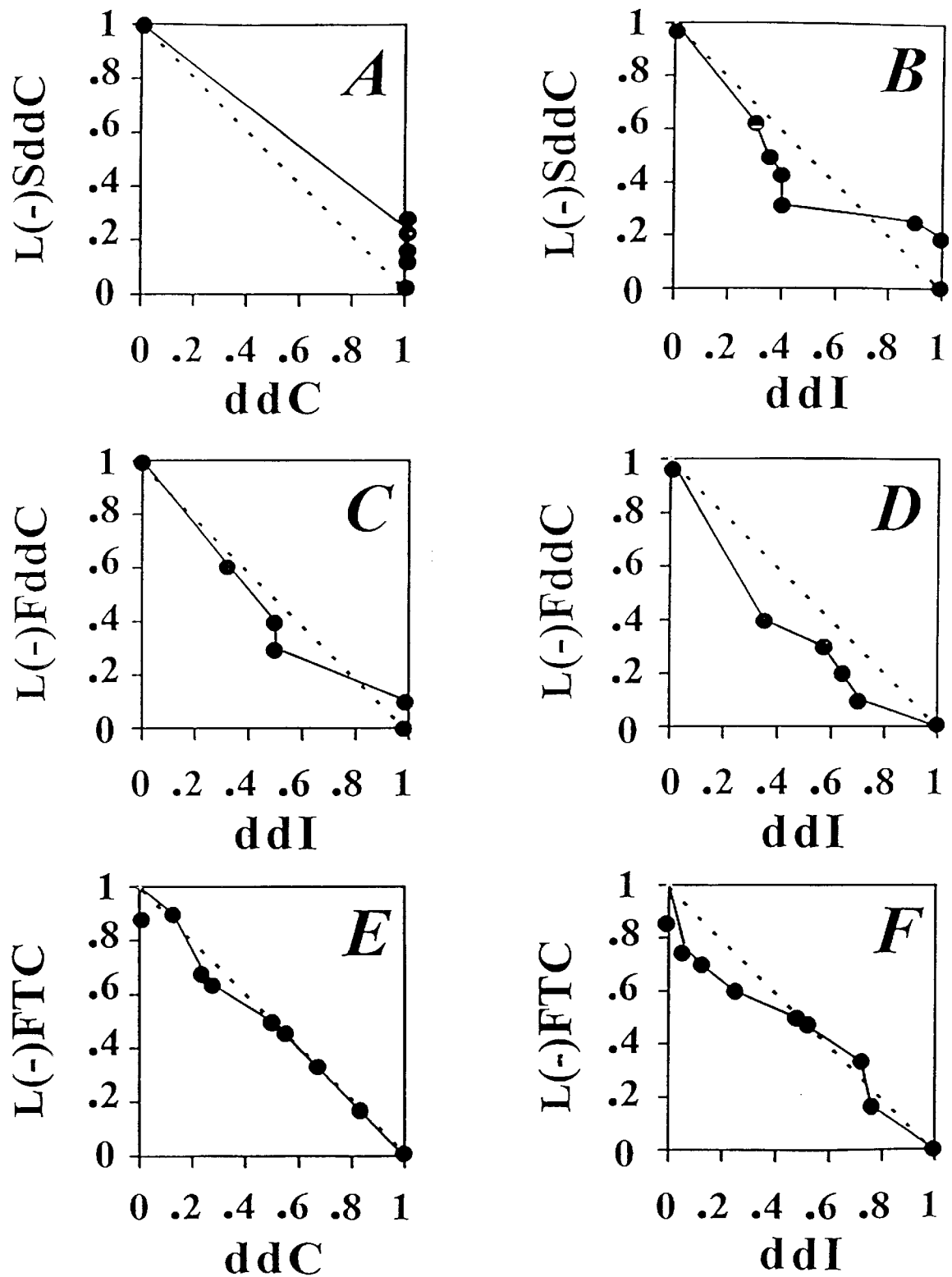
Figure 3:
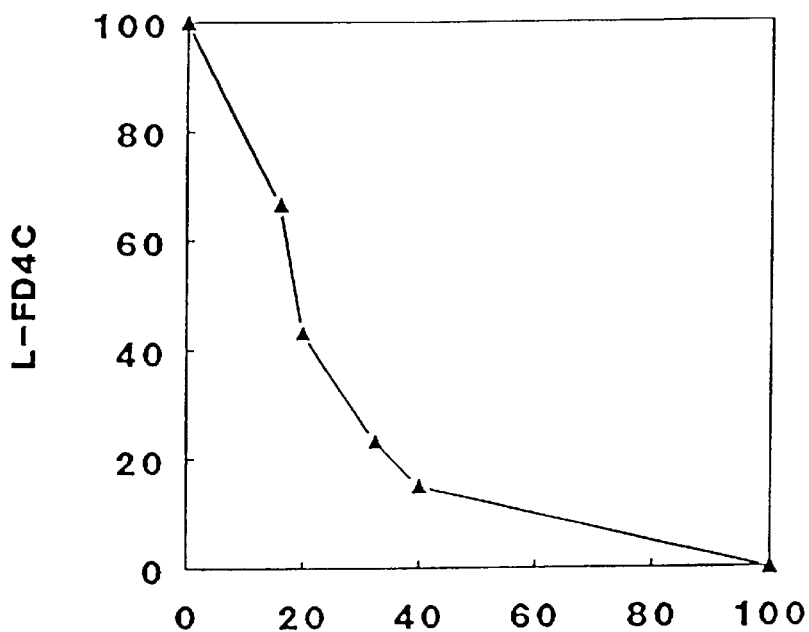
FIG. 3 is an isobologram depicting the effect of the co-administration of L-nucleosides (B-L-Fd4C or B-L-SddC or FTC) on the $ID_{50}$ value of ddC and ddI. In this figure, the isobolograms are plotted as the percent change in the $ID_{50}$ of ddC or ddI when in combination with L-nucleosides (B-L-FddC or B-L-SddC or B-L-FTC) plotted against the percent change in the $ID_{50}$ value of L-nucleosides when in combination with ddC or ddI.
Figure 3:
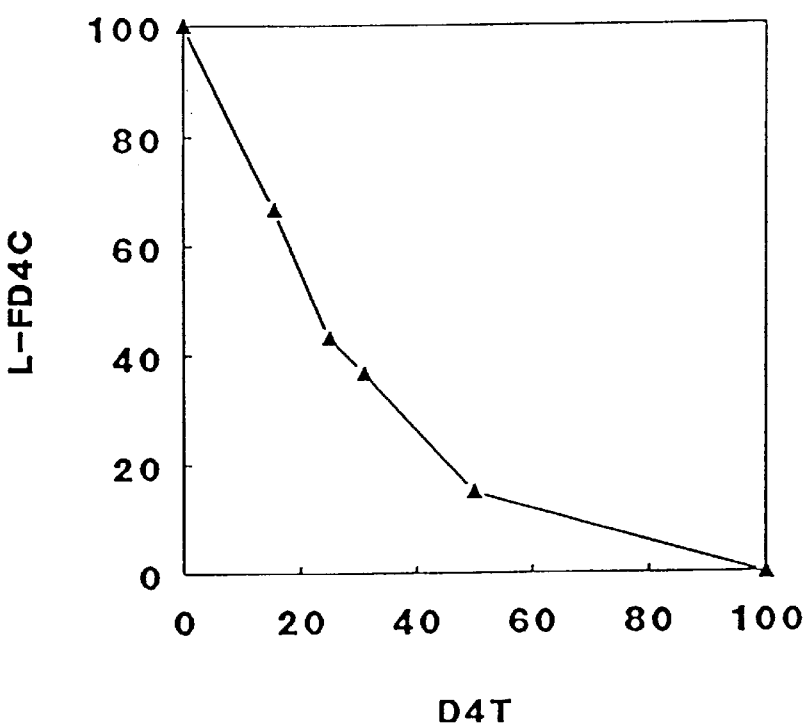
Figure 1:
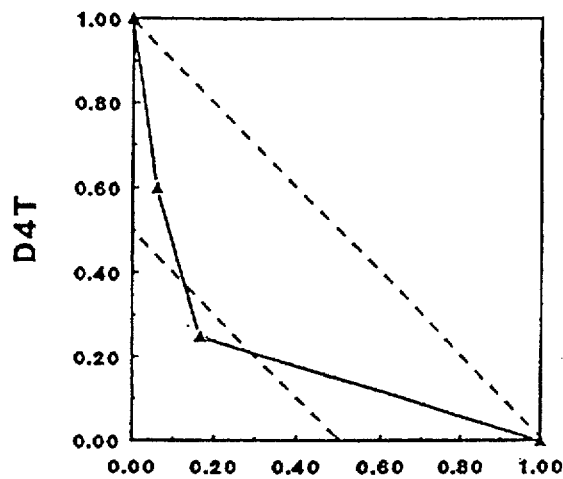
Figure 1:
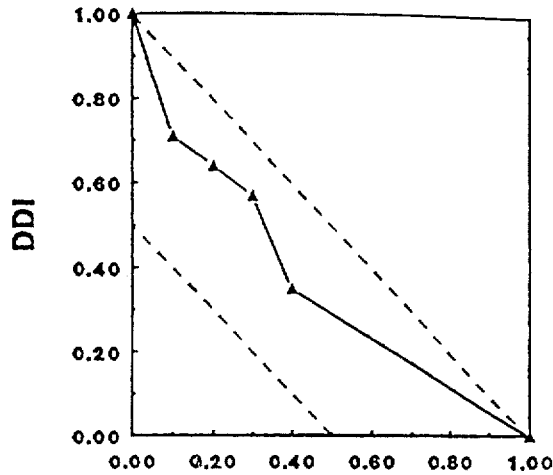
Figure 1:
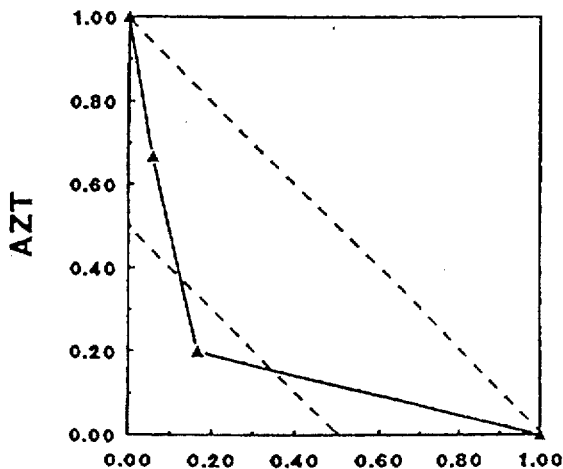
Figure 1:
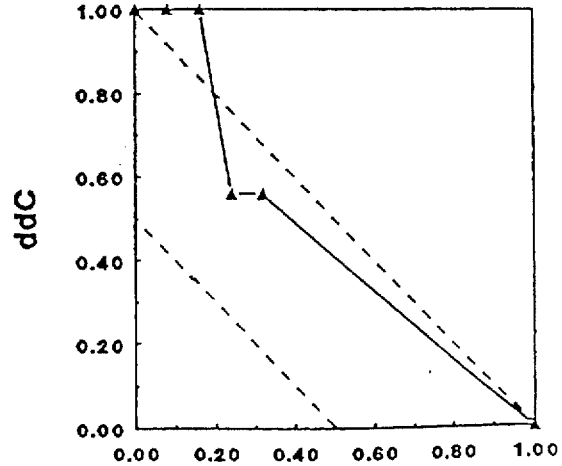

In the Figures:

Delete Figures 1-3 and insert attached Figure 1.

Signed and Sealed this

Twenty-eighth Day of September, 1999

Attest:

Q. TODD DICKINSON

Attesting Officer

Acting Commissioner of Patents and Trademarks

ISOBOLOGRAM
Percent of ID$_{50}$

L(-)FddC

UNITED STATES PATENT AND TRADEMARK OFFICE
CERTIFICATE OF CORRECTION

PATENT NO. : 5,869,461
DATED : February 9, 1999
INVENTOR(S) : Yung-Chi Cheng and Tai-Shun Lin It is certified that error appears in the above-identified patent and that said Letters Patent is hereby corrected as shown below:

Column 1,
Line 3, insert:
-- The invention identified above is a subject invention under 35 U.S.C. 200, et seq., and the Standard Patent Rights Clause at 37 C.F.R. 401.14 or F.A.R. 52.227-11, which are included among the terms of NIH Grant Numbers CA 44358 and AI 32766. The government retains rights in the invention. --

Signed and Sealed this

Thirteenth Day of April, 2004

JON W. DUDAS
*Acting Director of the United States Patent and Trademark Office*